US006313110B1

(12) United States Patent
DeLucca

(10) Patent No.: US 6,313,110 B1
(45) Date of Patent: Nov. 6, 2001

(54) SUBSTITUTED 2H-1,3-DIAZAPIN-2-ONE USEFUL AS AN HIV PROTEASE INHIBITOR

(75) Inventor: George V. DeLucca, Wilmington, DE (US)

(73) Assignee: Dupont Pharmaceuticals Company, Wilmington, DE (US)

( * ) Notice: Subject to any disclaimer, the term of this patent is extended or adjusted under 35 U.S.C. 154(b) by 0 days.

(21) Appl. No.: 09/585,171

(22) Filed: Jun. 1, 2000

Related U.S. Application Data

(60) Provisional application No. 60/137,076, filed on Jun. 2, 1999.

(51) Int. Cl.$^7$ .......................... C07D 243/08; A61K 31/55
(52) U.S. Cl. ............................................. 514/218; 540/492
(58) Field of Search .............................. 540/492; 514/218

(56) References Cited

U.S. PATENT DOCUMENTS

| | | | |
|---|---|---|---|
| 4,644,055 | 2/1987 | Kettner et al. | 530/330 |
| 4,652,552 | 3/1987 | Kettner et al. | 514/18 |
| 4,749,681 | 6/1988 | Evers et al. | 512/8 |
| 5,276,049 | 1/1994 | Himmelsbach et al. | 514/392 |
| 5,532,356 | * 7/1996 | Smyser et al. | 540/492 |
| 5,532,357 | * 7/1996 | Rodgers et al. | 540/492 |
| 5,559,110 | * 9/1996 | Aungst | 514/218 |
| 5,610,294 | * 3/1997 | Lam et al. | 540/492 |
| 5,683,999 | * 11/1997 | Jadhav et al. | 514/218 |

FOREIGN PATENT DOCUMENTS

| | | |
|---|---|---|
| 001284 | 4/1979 | (EP) . |
| 443848 | 8/1991 | (EP) . |
| 589322 | 9/1992 | (EP) . |
| 61106532 | 5/1986 | (JP) . |
| 8707836 | 12/1987 | (WO) . |
| 8910752 | 11/1989 | (WO) . |
| 9004588 | 3/1990 | (WO) . |
| 9209297 | 6/1992 | (WO) . |
| 9221647 | 12/1992 | (WO) . |
| 9307128 | 4/1993 | (WO) . |
| 9408977 | 4/1994 | (WO) . |

OTHER PUBLICATIONS

Kempf et al., J. Med. Chem. (1990) 33:2687–2689.
Wittneberger et al., Tetrahedron (1993) 49:1547–1556.
Chemical Abstracts, 1987–1991 Chemical Substance Index, pp. 28157CS, 28906CS, 32617CS and 78099CS.
Lam et al., Science (1994) 263:380–384.
Ghosh et al. Tet. Letters (1991) 32:5729–5732.
Mitsuya and Broder, Nature (1987) 325:773–778.
Moore et al., Biochem. Biophys. Res. Comm. (1989) 159:420–425.
Orszanska and Rulko, Polish J. Chem. (1982) 56–1287–1296.
Kempf et al., J. Org. Chem. (1992) 57–5692–5700.
Newlander et al., J. Med. Chem. (1993) 36–2321–2331.
Chenera et al., Bioorganic & Med. Chem. Lett. (1993) 3:2717–2722.
Kondo et al., J. Antibiot. (1996) 19(3): 137–138.
Kefurt et al., Collect. Czech. Chem. Commun. (1984) 49(11):2665–2673.
Van Dam et al., Carbohydr. Res. (1989) 187(1):25–34.
Hirama et al., J. Am. Chem. Soc. (1985) 107:1797–1798.
Kano et al., Chem. Pharm. Bull. (1985) 33(1):340–346.
Moriconi et al., J. Org. Chem. (1972) 37(2):208–214.
Wuts et al., J. Org. Chem. (1991) 56:365–372.
Mailard et al. Chim. Ther. (1968) 3:321–324.
Zigeuner et al. Monats. Chem. (1961) 92:79–87.
Shono et al. Tetrahedron Lett. (1989) 30:1253–1256.
Marshall et al. J. Org. Chem. (1979) 44:1391–1397.
Bardili et al. Liebigs Ann. Chem. (1985) 275–300.
Seebach et al. Tetrahedron Lett. (1987) 28:3103–3106.
Lewis et al. Tetrahedron Lett. (1987) 28:5129–5232.
Rousn et al J. Org. Chem. (1982) 47–1371–1373.
Patel et al (Bioorg. Med. Chem. Lett. (1999), 9(22), 3217–3220).
Patel et al. (Bioorg. Med Chem. Lett. (1999), 9(22), 3217–3220).*
De Lucca et al. (J. Med. Chem. (1998), 41(13), 2411–2423).*

* cited by examiner

Primary Examiner—Bruck Kifle

(57) ABSTRACT

The present invention relates to a compound of Formula (I):

(I)

or pharmaceutically acceptable salt forms or prodrugs thereof, which are useful as inhibitors of HIV protease, and to pharmaceutical compositions and diagnostic kits comprising the same, and methods of using the same for treating viral infection or as an assay standard or reagent.

3 Claims, No Drawings

SUBSTITUTED 2H-1,3-DIAZAPIN-2-ONE USEFUL AS AN HIV PROTEASE INHIBITOR

This application claims the benefit of U.S. Provisional Application No. 60/137,076 filed Jun. 2, 1999.

FIELD OF THE INVENTION

This invention relates generally to a 1-(3-aminophenyl)-3-(1H-indazol-5-ylmethyl)-substituted 2H-1,3-diazapin-2-one which is useful as an inhibitor of HIV protease, pharmaceutical compositions and diagnostic kits comprising the same, and methods of using the same for treating viral infection or as assay standards or reagents.

BACKGROUND OF THE INVENTION

Two distinct retroviruses, human immunodeficiency virus (HIV) type-1 (HIV-1) or type-2 (HIV-2), have been etiologically linked to the immunosuppressive disease, acquired immunodeficiency syndrome (AIDS). HIV seropositive individuals are initially asymptomatic but typically develop AIDS related complex (ARC) followed by AIDS. Affected individuals exhibit severe immunosuppression which predisposes them to debilitating and ultimately fatal opportunistic infections.

The disease AIDS is the end result of an HIV-1 or HIV-2 virus following its own complex life cycle. The virion life cycle begins with the virion attaching itself to the host human T-4 lymphocyte immune cell through the bonding of a glycoprotein on the surface of the virion's protective coat with the CD4 glycoprotein on the lymphocyte cell. Once attached, the virion sheds its glycoprotein coat, penetrates into the membrane of the host cell, and uncoats its RNA. The virion enzyme, reverse transcriptase, directs the process of transcribing the RNA into single-stranded DNA. The viral RNA is degraded and a second DNA strand is created. The now double-stranded DNA is integrated into the human cell's genes and those genes are used for cell reproduction.

At this point, the human cell carries out its reproductive process by using its own RNA polymerase to transcribe the integrated DNA into viral RNA. The viral RNA is translated into the precursor gag-pol fusion polyprotein. The polyprotein is then cleaved by the HIV protease enzyme to yield the mature viral proteins. Thus, HIV protease in responsible for regulating a cascade of cleavage events that lead to the virus particle's maturing into a virus that is capable of full infectivity.

The typical human immune system response, killing the invading virion, is taxed because a large portion of the virion's life cycle is spent in a latent state within the immune cell. In addition, viral reverse transcriptase, the enzyme used in making a new virion particle, is not very specific, and causes transcription mistakes that result in continually changed glycoproteins on the surface of the viral protective coat. This lack of specificity decreases the immune system's effectiveness because antibodies specifically produced against one glycoprotein may be useless against another, hence reducing the number of antibodies available to fight the virus. The virus continues to reproduce while the immune response system continues to weaken. Eventually, the HIV largely holds free reign over the body's immune system, allowing opportunistic infections to set in and without the administration of antiviral agents, immunomodulators, or both, death may result.

There are at least three critical points in the virus's life cycle which have been identified as possible targets for antiviral drugs: (1) the initial attachment of the virion to the T-4 lymphocyte or macrophage site, (2) the transcription of viral RNA to viral DNA (reverse transcriptase, RT), and (3) the assemblage of the new virus particle during reproduction (e.g., HIV aspartic acid protease or HIV protease).

The genomes of retroviruses encode a protease that is responsible for the proteolytic processing of one or more polyprotein precursors such as the pol and gag gene products. See Wellink, *Arch. Virol.* 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., *J. Virol.* 53 899 (1985); Katoh et al., *Virology* 145 280 (1985). Therefore, retroviral protease inhibition provides an attractive target for antiviral therapy. See Mitsuya, *Nature* 325 775 (1987).

The ability to inhibit a viral protease provides a method for blocking viral replication and therefore a treatment for viral diseases, such as AIDS, that may have fewer side effects, be more efficacious, and be less prone to drug resistance when compared to current treatments. As a result, numerous HIV protease inhibitors are already either in clinical development, in clinical trials or on the market; for example Roche's saquinavir, Abbott's ritonavir, Merck's indinavir, Agouron's nelfinavir, Vertex's VX-478, Japan Energy's KNI-272, and Ciba-Geigy's CGP 61755.

As evidenced by the protease inhibitors presently marketed and in clinical trials, a wide variety of compounds have been studied as potential HIV protease inhibitors. One core, cyclic ureas, has received significant attention. For example, in PCT Application Number WO94/19329, Lam et al generically describe cyclic ureas of the formula:

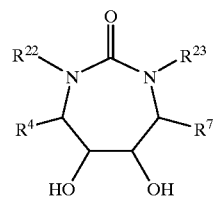

and methods of preparing these ureas. Cyclic ureas are also disclosed by Lam et al in U.S. Pat. No. 5,610,294 and U.S. Pat. No. 5,811,422. Though the present compound falls within the description of Lam et al, it is not specifically disclosed therein.

Even with the current success of protease inhibitors, it has been found that HIV patients can become resistant to a single protease inhibitor. Thus, it is desirable to develop additional protease inhibitors to further combat HIV infection.

SUMMARY OF THE INVENTION

Accordingly, one object of the present invention is to provide a novel protease inhibitor.

It is another object of the present invention to provide pharmaceutical compositions with protease inhibiting activity comprising a pharmaceutically acceptable carrier and a therapeutically effective amount of the compound of the present invention or a pharmaceutically acceptable salt or prodrug form thereof.

It is another object of the present invention to provide a novel method for treating HIV infection which comprises administering to a host in need of such treatment a therapeutically effective amount of the compound of the present invention or a pharmaceutically acceptable salt or prodrug form thereof.

It is another object of the present invention to provide a novel method for treating HIV infection which comprises administering to a host in need thereof a therapeutically effective combination of (a) the compound of the present invention and (b) one or more compounds selected from the group consisting of an HIV reverse transcriptase inhibitor, an HIV protease inhibitor, and an AIDS antiviral.

It is another object of the present invention to provide a method of inhibiting HIV present in a body fluid sample which comprises treating the body fluid sample with an effective amount of a compound of the present invention.

It is another object of the present invention to provide a kit or container containing the compound of the present invention in an amount effective for use as a standard or reagent in a test or assay for determining the ability of a potential pharmaceutical to inhibit HIV protease, HIV growth, or both.

These and other objects, which will become apparent during the following detailed description, have been achieved by the discovery that compound of Formula (I):

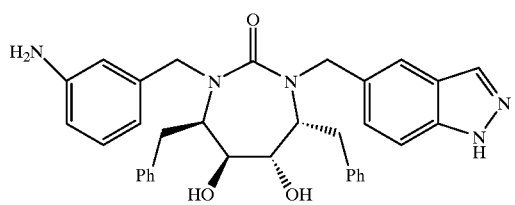

(I)

or pharmaceutically acceptable salts or prodrug forms thereof, is an effective HIV protease inhibitor.

DETAILED DESCRIPTION OF PREFERRED EMBODIMENTS

Thus, in a first embodiment, the present invention provides a novel compound of Formula (I):

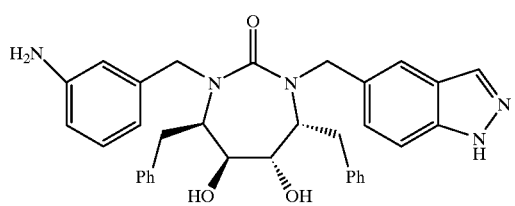

(I)

or a pharmaceutically acceptable salt or prodrug form thereof.

In a second embodiment, the present invention provides a novel pharmaceutical composition comprising a pharmaceutically acceptable carrier and a therapeutically effective amount of a compound of Formula (I) or a pharmaceutically acceptable salt or prodrug form thereof.

In a third embodiment, the present invention provides a novel method for treating HIV infection which comprises administering to a host in need of such treatment a therapeutically effective amount of a compound of Formula (I) or a pharmaceutically acceptable salt or prodrug form thereof.

In a fourth embodiment, the present invention provides a novel method of treating HIV infection which comprises administering, in combination, to a host in need thereof a therapeutically effective amount of:
(a) a compound of Formula (I); and,
(b) at least one compound selected from the group consisting of an HIV reverse transcriptase inhibitor, an HIV protease inhibitor, and an AIDS antiviral.

In a preferred embodiment the reverse transcriptase inhibitor is a nucleoside reverse transcriptase inhibitor.

In a more preferred embodiment the nucleoside reverse transcriptase inhibitor is selected from AZT, 3TC, ddI, ddC, and d4T.

In an even more preferred embodiment the nucleoside reverse transcriptase inhibitor is selected from AZT and 3TC.

In an even furthermore preferred embodiment the nucleoside reverse transcriptase inhibitor is AZT.

In another preferred embodiment the reverse transcriptase inhibitor is a non-nucleoside reverse transcriptase inhibitor.

In a more preferred embodiment the non-nucleoside reverse transcriptase inhibitor is efavirenz.

In another preferred embodiment the protease inhibitor is selected from saquinavir, ritonavir, indinavir, VX-478, nelfinavir, KNI-272, CGP-61755, and U-103017.

In a more preferred embodiment the protease inhibitor is selected from saquinavir, ritonavir, nelfinavir, and indinavir.

In an even more preferred embodiment the protease inhibitor is indinavir.

In another more preferred embodiment, the reverse transcriptase inhibitor is selected from AZT, 3TC, ddI, ddC, d4T, and efavirenz, and the protease inhibitor is selected from saquinavir, ritonavir, indinavir, VX-478, and nelfinavir.

In a more preferred embodiment, the reverse transcriptase inhibitor is selected from AZT, 3TC, and efavirenz, and the protease inhibitor is selected from saquinavir, ritonavir, nelfinavir, and indinavir.

In a fifth embodiment, the present invention provides a pharmaceutical kit useful for the treatment of HIV infection, which comprises a therapeutically effective amount of:
(a) a compound of Formula (I); and,
(b) at least one compound selected from the group consisting of HIV reverse transcriptase inhibitors and HIV protease inhibitors, in one or more sterile containers.

In a sixth embodiment, the present invention provides a novel method of inhibiting HIV present in a body fluid sample which comprises treating the body fluid sample with an effective amount of a compound of Formula (I).

In a seventh embodiment, the present invention to provides a novel a kit or container comprising a compound of Formula (I) in an amount effective for use as a standard or reagent in a test or assay for determining the ability of a potential pharmaceutical to inhibit HIV protease, HIV growth, or both.

DEFINITIONS

As used herein, the following terms and expressions have the indicated meanings. It will be appreciated that the compound of the present invention contains an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

As used herein, "HIV reverse transcriptase inhibitor" is intended to refer to both nucleoside and non-nucleoside inhibitors of HIV reverse transcriptase (RT). Examples of nucleoside RT inhibitors include, but are not limited to, AZT, ddC, ddI, d4T, and 3TC. Examples of non-nucleoside RT inhibitors include, but are not limited to, efavirenz (DuPont Pharmaceuticals Co.), rescriptor (delavirdine, Pharmacia and Upjohn), viviradine (Pharmacia and Upjohn U90152S), TIBO derivatives, BI-RG-587, nevirapine, L-697,661, LY 73497, and Ro 18,893 (Roche). Additional examples of non-nucleoside RT inhibitors include compounds disclosed in WO98/45276 published Oct. 15, 1998; the contents of which are also disclosed in copending and commonly assigned U.S. patent application Ser. No. 09/056,820, filed Apr. 8, 1998, the contents of which are hereby incorporated by reference.

As used herein, "HIV protease inhibitor" is intended to refer to compounds which inhibit HIV protease. Examples include, but are not limited to, saquinavir (Roche, Ro31-8959), ritonavir (Abbott, ABT-538), indinavir (Merck, MK-639), VX-478 (Vertex/Glaxo Wellcome), nelfinavir (Agouron, AG-1343), KNI-272 (Japan Energy), CGP-61755 (Ciba-Geigy), DMP450 (DuPont Pharmaceuticals Co.), and U-103017 (Pharmacia and Upjohn). Additional examples include the cyclic protease inhibitors disclosed in WO93/07128, WO 94/19329, WO 94/22840, and PCT Application Ser. No. US96/03426; as well as the protease inhibitors disclosed in WO94/04993, WO95/33464, WO96/28,418, and WO96/28,464.

As used herein, an "AIDS antiviral" is intended to refer to compounds which prevent or treat the consequent pathological condition or conditions of HIV known as AIDS. Examples of AIDS antivirals are disclosed in U.S. Pat. No. 5,811,423, the contents of which are hereby incorporated by reference.

As used herein, "pharmaceutically acceptable salts" refer to derivatives of the disclosed compound wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of the compound with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

"Prodrugs" are intended to include any covalently bonded carriers which release the active parent drug according to Formula (I) or other formulas or compounds of the present invention in vivo when such prodrug is administered to a mammalian subject. Prodrugs of a compound of the present invention, for example Formula (I), are prepared by modifying functional groups present in the compound in such a way that the modifications are cleaved, either in routine manipulation or in vivo, to the parent compound. Prodrugs include compounds of the present invention wherein the hydroxy or amino group is bonded to any group that, when the prodrug is administered to a mammalian subject, cleaves to form a free hydroxyl or free amino, respectively. Examples of prodrugs include, but are not limited to, acetate, formate, or benzoate derivatives of alcohol and amine functional groups in the compound of Formula (I); phosphate esters, dimethylglycine esters, aminoalkylbenzyl esters, aminoalkyl esters and carboxyalkyl esters of alcohol functional groups in the compound of Formula (I); and the like. Additional examples include compounds wherein the two hydroxy groups of Formula (I) join to form an epoxide; —OCH$_2$SCH$_2$O—; —OC(=O)O—; —OCH$_2$O—; —OC(=S)O—; —OC(=O)C(=O)O—; —OC(CH$_3$)$_2$O—; —OC((CH$_2$)$_3$NH$_2$)(CH$_3$)O—; —OC(OCH$_3$)(CH$_2$CH$_2$CH$_3$)O—; or —OS(=O)O—.

"Stable compound" and "stable structure" are meant to indicate a compound that is sufficiently robust to survive isolation to a useful degree of purity from a reaction mixture, and formulation into an efficacious therapeutic agent. Only stable compounds are contemplated by the present invention.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention or an amount of the combination of compounds claimed effective to inhibit HIV infection or treat the symptoms of HIV infection in a host. The combination of compounds is preferably a synergistic combination. Synergy, as described for example by Chou and Talalay, Adv. Enzyme Regul. 22:27–55 (1984), occurs when the effect (in this case, inhibition of HIV replication) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased antiviral effect, or some other beneficial effect of the combination compared with the individual components.

Other features of the invention will become apparent in the course of the following descriptions of exemplary embodiments which are given for illustration of the invention and are not intended to be limiting thereof.
Synthesis
The synthesis of the compound of the invention is summarized in Scheme 1:
SCHEME 1
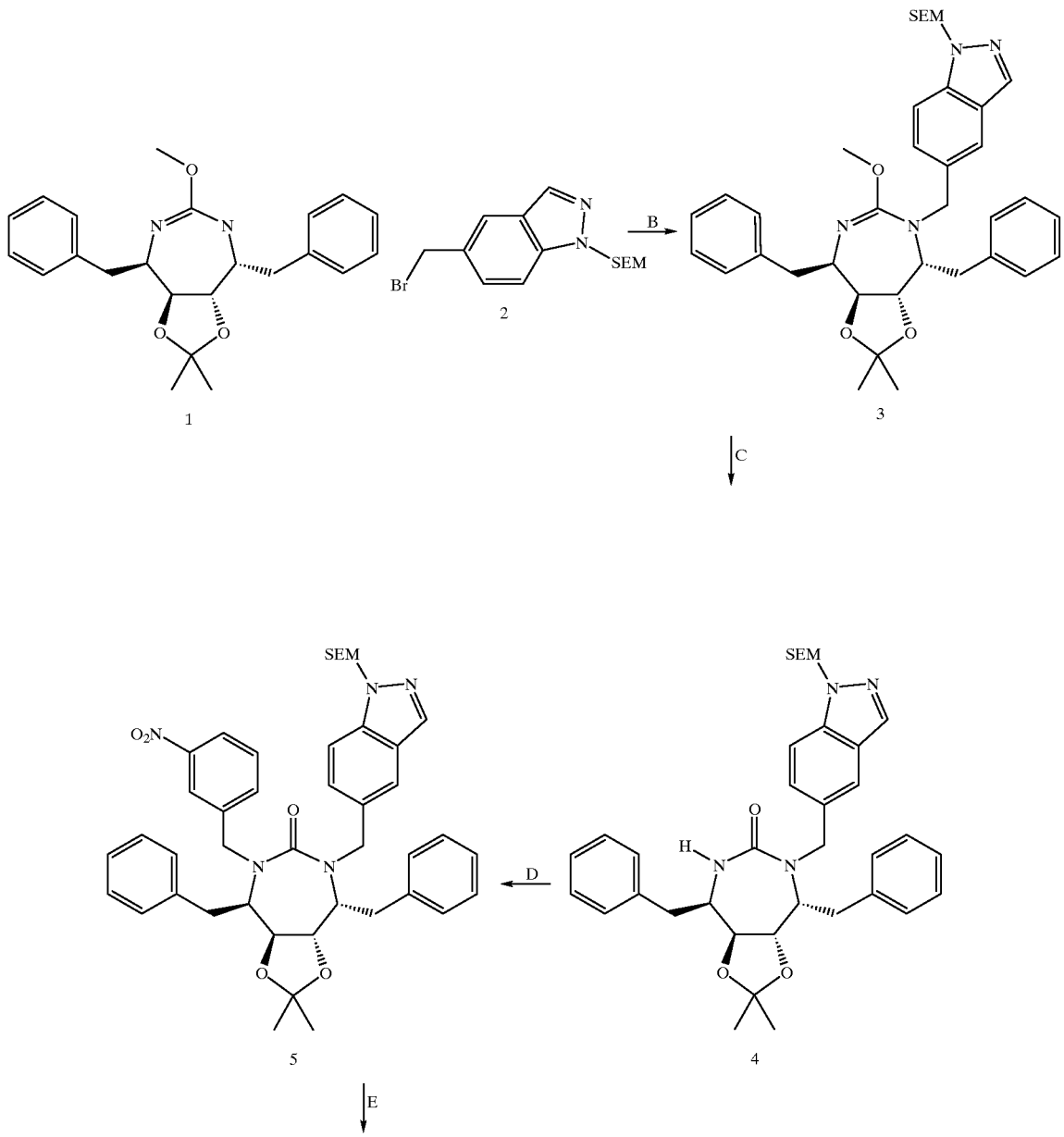

-continued
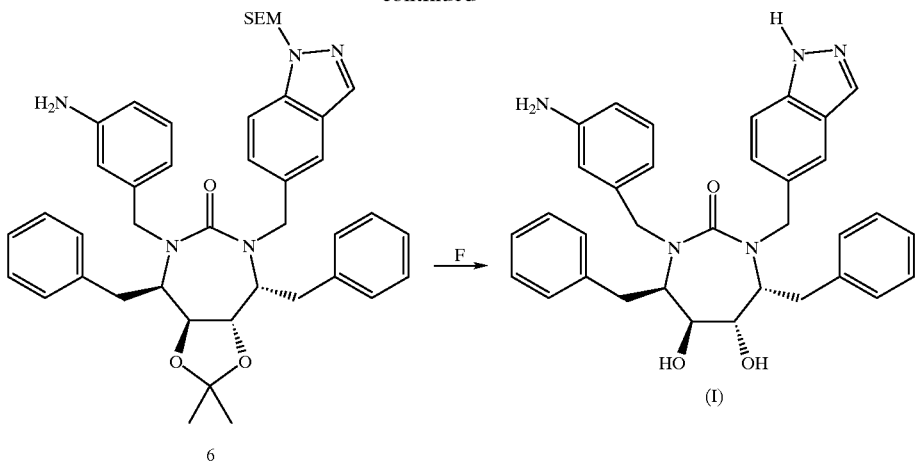
SCHEME 2
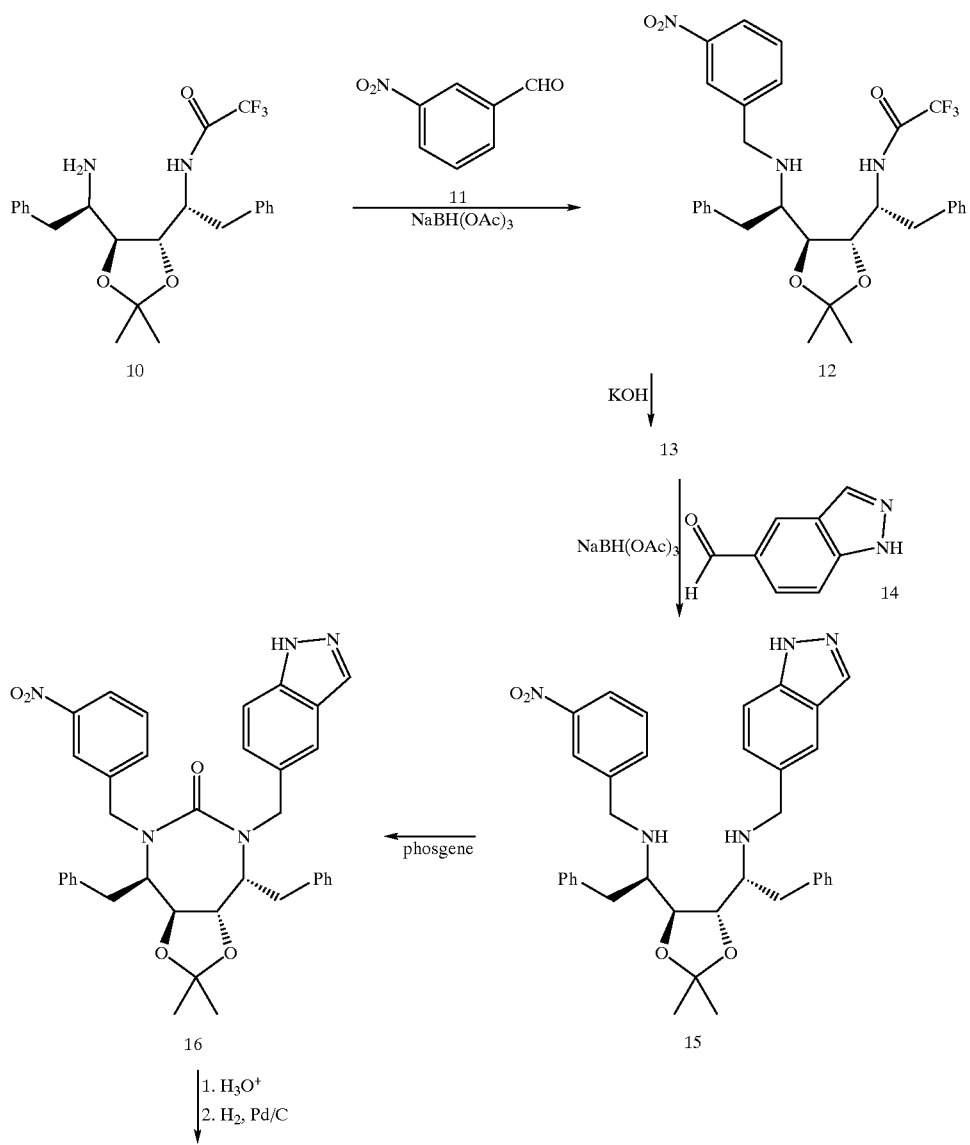

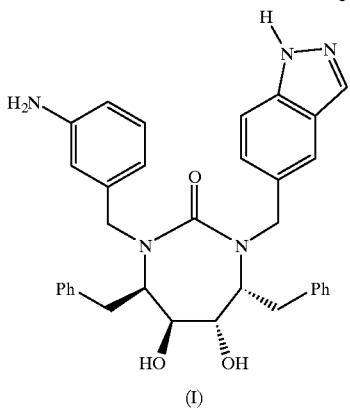

(I)

Alternatively, the compound of Formula (I) can be prepared according to the procedure of Scheme 2. In Scheme 2 the starting material of compound 10 can be prepared by known methods. For example, preparation of compound 10 is shown in Scheme 2 of PCT application WO99/18085 published Apr. 15, 1999, the contents of which are hereby incorporated by reference. The preparation of compound 10 is also disclosed copending and commonly assigned U.S. patent application U.S. Ser. No. 09/166,507, filed Oct. 5, 1998, the contents of which are hereby incorporated by reference.

EXAMPLES

Abbreviations used in the Examples are defined as follows: "° C." for degrees Celsius, "d" for doublet, "dd" for doublet of doublets, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, and "TLC" for thin layer chromatography.

Example 1

Preparation of (4R,5S,6S,7R)-hexahydro-1-[(indazol-5-yl)methyl]-5,6-dihydroxy-4,7-bis[phenylmethyl]-3-(3-aminophenyl)methyl-2H-1,3-diazapin-2-one (I).

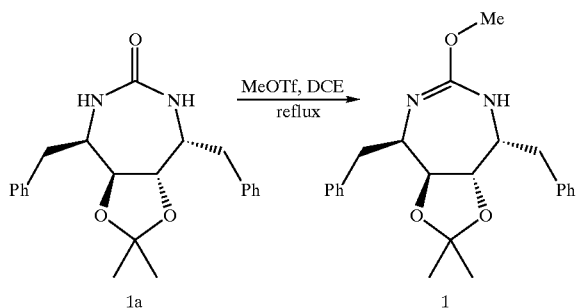

Compound 1a can be prepared by known methods. For example, preparation of compound 1 is shown in Scheme 1 of Rossano et al (*Tetr. Lett.* 1995, 36(28), 4967, 4968), the contents of which are hereby incorporated by reference. An additional method of preparation of compound 1a is shown in Example 6 of U.S. Pat. No. 5,530,124, the contents of which are hereby incorporated by reference. An additional method of preparation of compound 1 is shown in Example 3 of U.S. Pat. No. 5,532,357, the contents of which are hereby incorporated by reference.

PART A:

To a suspension of compound 1a (10.0 g; 27.3 mmol) in 1,2-dichloroethane (100 mL) was added methyltriflate (3.4 mL, 30 mmol). After refluxing overnight, the reaction was washed with saturated NaHCO$_3$, saturated NaCl, dried (Na$_2$SO$_4$) and evaporated leaving 12.5 g of a yellow oil. Column chromatography (flash SiO$_2$; 25% EtOAc/hexane) gave 7.86 g of compound 1 as a pale yellow oil which crystallized on standing (75% yield). m.p.=97–100° C. MH$^+$=381.

PART B:

Preparation of isourea 3.

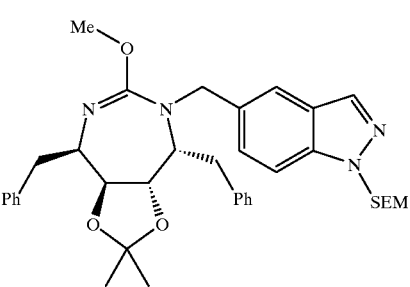

3

A solution of isourea 1 (1.49 g, 3.90 mmol) and 5-(bromomethyl)-1-SEM-indazole 2 (2.0 g, 5.86 mmol) in dry THF (40 mL) was cooled in an ice bath and treated drop-wise with potassium t-butoxide (4.60 mL; 1.0 M solution in THF). The mixture was stirred at 0° C. for 1 h. The reaction was quenched with 100 mL of water and the resulting suspension extracted into ethyl acetate (3×100 mL). The combined organic extracts were washed with water and brine. The organic extract was dried over Na$_2$SO$_4$, filtered and concentrated and the resulting residue was chromatographed (MPLC silica gel, 25% EtOAc/hexane) to give 1.98 g (79% yield) of the alkylated isourea product 3.

$^1$H NMR (CDCl$_3$) δ 8.02 (s, 1 H), 7.58 (d, J=8.8 Hz, 1H), 7.46–7.21 (m, 9 H), 7.05 (m, 1 H), 5.79 (s, 2 H), 4.57 (d, J=14 Hz, 1 H), 4.26–4.21 (m, 2 H), 4.15 (m, 1 H), 3.81 (m, 1 H), 3.63 (t, J=8.0 Hz, 2 H), 3.54 (s, 3 H), 3.35 (d, J=14 Hz, 1 H), 3.12–3.06 (m, 2 H), 2.95–2.87 (m, 2 H), 1.52 (s, 3 H), 1.51 (s, 3 H), 0.98–0.929 (m, 2 H), −0.01 (s, 9 H). CI-MS m/z =641.3 (M+H)⁺

PART C:

(4R,5S,6S,7R)-Hexahydro-1-[5-(1-SEM-indazole) methyl]-5,6-O-isopropylidene-4,7-bis-(phenylmethyl)-2H-1,3-diazapin-2-one (4).

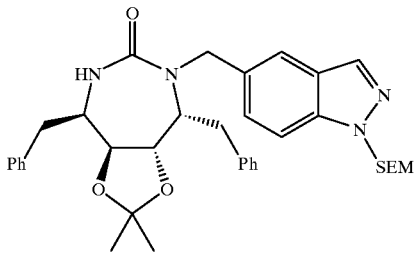

A solution of isourea 3 (17.0 g, 26.52 mmol) in 120 mL of toluene was treated with AcOH (1.91 g, 31.8 mmol) and the solution heated at reflux for 24 h. The solvent was removed in vacuo and the residue dissolved in ether. The ether solution was washed with water, saturated sodium bicarbonate and brine. The organic solution was dried, concentrated under vacuum and the resulting residue was chromatographed (MPLC silica gel, 20% EtOAc/hexane) to give 14.0 g (84% yield) of the mono-alkylated urea product 4.

¹H NMR (CDCl₃) δ 8.02 (s, 1 H), 7.50–7.31 (m, 12 H), 5.80 (s, 2 H), 5.28 (d, J=14 Hz, 1 H), 5.02 (d, J=6.6 Hz, 2 H), 4.35 (dd, J=10 Hz, J=5 Hz, 1 H), 3.93–3.84 (m, 2 H), 3.63 (t, J=8.0 Hz, 2 H), 3.62 (m, 1 H),3.21–3.07 (m, 4 H), 2.80 (m, 1 H), 1.54 (s, 3 H), 1.47 (s, 3 H), 0.99 −0.93 (m, 2 H), −0.01 (s, 9 H). MS m/z 627.5 (M+H)⁺, 100%.

PART D:

(4R,5S,6S,7R)-Hexahydro-1-[5-(1-SEM-indazole) methyl]-5,6-O-isopropylidene-4,7-bis-(phenylmethyl)-3-[(3-nitrophenyl)methyl]-2H-1,3-diazapin-2-one (5).

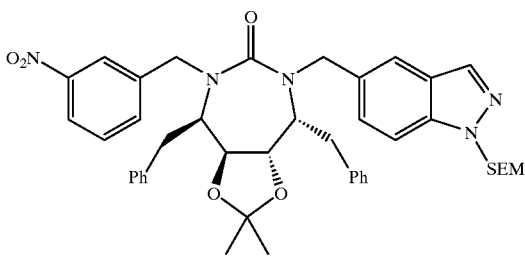

A solution of mono-alkylated urea 4 (3.50 g, 5.56 mmol) and 3-nitrobenzyl bromide (1.80 g, 8.34 mmol) in THF (60 mL) was cooled in an ice bath and treated drop-wise with potassium t-butoxide (8.3 mL; 1.0 M solution in THF). The mixture was stirred at 0° C. for 1 h. The reaction was quenched with 100 mL of water and the resulting suspension extracted into ethyl acetate (3×200 mL). The combined organic extracts were washed with water and brine, dried and concentrated. The resulting residue is chromatographed (MPLC silica gel, 25% EtOAc/hexane) to give 3.93 g (90% yield) of the dialkylated urea 5 as a solid.

¹H NMR (CDCl₃) δ 8.18 (d, J=8.0 Hz, 1 H), 8.13 (s, 1 H), 8.05 (s, 1 H), 7.64–7.52 (m, 3 H), 7.43–7.34 (m, 8 H), 7.15–7.12 (m, 4 H), 5.80 (s, 2 H), 5.09 (d, J=14 Hz, 1 H), 4.93 (d, J=14 Hz, 1 H), 4.11 (m, 1 H), 3.97–3.86 (m, 3 H), 3.63 (t, J=8.0 Hz, 2 H), 3.50 (d, J=14 Hz, 1 H), 3.30 (d, J=14 Hz, 1 H), 3.14–2.93 (m, 4 H), 1.49 (s, 3 H), 1.44 (s, 3 H), 0.95 (t, J=8.0 Hz, 2 H), −0.01 (s, 9 H). CI-MS m/z 762 (M+H)⁺, 55%.

PART E:

(4R,5S,6S,7R)-Hexahydro-1-[5-(1-SEM-indazole) methyl]-5,6-O-isopropylidene- 4,7-bis-(phenylmethyl)-3-[(3-aminophenyl)methyl]-2H-1,3-diazapin-2-one (6).

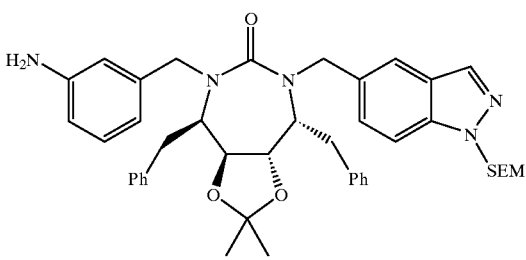

A solution of nitro 5 (1.62 g, 2.12 mmol) in 60 mL of THF was treated with 10% Pd/C (0.8 g) and was hydrogenated at 50 psi for 40 min. The resulting solution was filtered and the solvent removed under vacuum to give the aniline 6 (1.55 g, 100% yield).

¹H NMR (CDCl₃) δ 8.04 (s, 1 H), 7.59 (d, J=8.0 Hz, 1 H), 7.46–7.14 (m, 13 H), 6.68–6.64 (m, 2 H), 6.48 (bs, 1 H), 5.80 (s, 2 H), 5.12 (d, J=14 Hz, 1 H), 5.03 (d, J=14 Hz, 1 H), 3.93–3.89 (m, 4 H), 3.71–3.60 (m, 4 H), 3.34 (d, J =14 Hz, 1 H), 3.10 −2.99 (m, 5 H), 1.43 (s, 3 H), 1.41 (s, 3 H), 0.95 (t, J=8.0 Hz, 2 H), −0.01 (s, 9 H).

PART F:

(4R,5S,6S,7R)-hexahydro-1-[(indazol-5-yl)methyl]-5,6-dihydroxy-4,7-bis[phenylmethyl]-3-(3-aminophenyl) methyl-2H-1,3-diazapin-2-one (I).

(I)

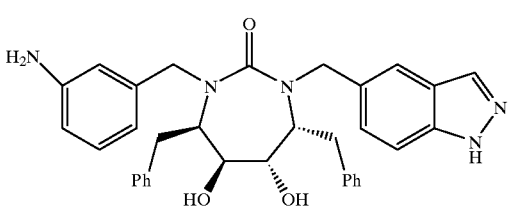

A solution of dialkylated urea 6 (1.5 g, 2.05 mmol) in MeOH (5 ml) was treated with 5 ml solution of 4 N HCl in dioxane and the resulting mixture was heated at reflux for 8 h. The solvent was removed under vacuum and the residue was suspended in 100 mL of saturated sodium bicarbonate and extracted into ethyl acetate. The organic extracts were washed with water, saturated sodium bicarbonate and brine. The organic solution was dried, concentrated under vacuum and the resulting residue was chromatographed (MPLC silica gel, 7% MeOH/CH₂Cl₂) to give 1.0 g (87% yield) of (I) as a white solid. mp 134–136° C. ¹H NMR (DMSO-D₆) δ 13.03 (bs, 1 H), 8.05 (s, 1 H), 7.51 (d, J=8 Hz, 2 H), 7.36–7.19 (m, 8 H), 7.13 (d, J=8 Hz, 2 H), 7.01 (d, J=8 Hz, 2 H), 6.94 (t, J=8 Hz, 1 H), 6.42 (d, J=8 Hz, 1 H), 6.33 (s, 1 H), 6.23 (d, J=8 Hz, 1 H), 5.07 (bs, 2 H), 5.00 (bs , 2 H), 4.79 (d, J=14 Hz, 1 H), 4.61 (d, J=14 Hz, 1 H), 3.55–3.35 (m, 4 H), 3.00–2.80 (m, 5 H), 2.59 (d, J=14 Hz, 1 H). ESIMS m/z 562 (M+H⁺100%). HRMS Calcd for C₃₄H₃₆N₅O₃ (M+H⁺):

562.2818, found: 562.2807. Anal. Calc for C$_{34}$H$_{35}$N$_5$O$_3$.H$_2$O): C, 70.45; H, 6.43; N, 12.09. Found: C, 70.60; H, 6.31; N, 11.99.

Example 2

Preparation of (4R,5S,6S,7R)-hexahydro-1-[(indazol-5-yl)methyl]-5,6-dihydroxy-4,7-bis[phenylmethyl]-3-(3-aminophenyl)methyl-2H-1,3-diazapin-2-one (I).

PART A:

Preparation of compound 10.

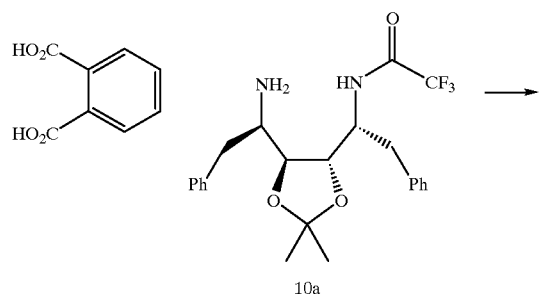

10a

Compound 10a can be prepared by known methods. For example, preparation of compound 10a is shown in PCT application WO99/18085 published April 15, 1999, the contents of which are hereby incorporated by reference. The preparation of compound 10a is also disclosed in copending and commonly assigned U.S. patent application U.S. Ser. No. 09/166507, filed Oct. 5, 1998, the contents of which are hereby incorporated by reference.

A flask containing 10a (602.6 g), water (2.00 L), and toluene (2.15 L) was charged with a solution of sodium hydroxide (83.6 g) in water (0.15 L). The mixture was stirred for 0.5 h and the layers separated. The toluene layer was dried by azeotropic distillation at 110° C. under nitrogen until all water had been removed (the distillate had become clear). The solution was diluted to a total volume of 4.00 L to prepare a stock solution containing 109 g of 10 per liter of solution, assuming quantitative conversion.

Part B:
Preparation of 12

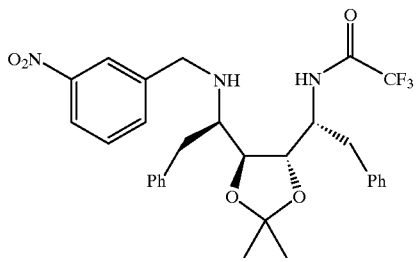

A flask containing 10 (196 g), 2-nitrobenzaldehyde (71 g), and toluene (2.00 L) was heated under nitrogen to reflux at 110° C. and the water formed removed by a Dean-Stark trap. After 80 minutes, water production had halted and the solution was cooled to 30° C. Sodium triacetoxyborohydride (143 g) was charged and the mixture stirred overnight at ambient temperature. Water was charged to quench the remaining hydride and the layers separated. The organic layer was washed with water (500 mL) and concentrated by rotary evaporation to an oil. This oil was dissolved into cyclohexane (2.50 L) and heated to 70° C. A solution of methanesulfonic acid (43.2 g) in 2-propanol (0.45 L) was added over 50 minutes. The mixture was cooled to 10° C. and the solids collected by filtration. The solids were dried under high vacuum to produce 307.6 g of 12 (97% yield). HNMR spectroscopy revealed 5 wgt % of cyclohexane.

PART C:
Preparation of 13.

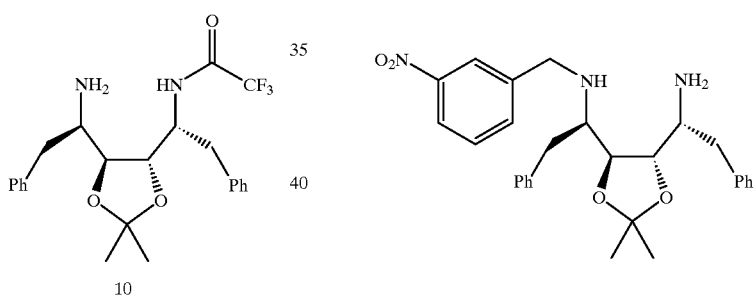

A flask containing 12 (232.2 g) in 2-propanol (0.49 L) was charged with a solution of potassium hydroxide (74.2 g) in water (0.167 L). This was heated to reflux at 78° C. and held 2 h. Water (0.49 L) and toluene (0.49 L) was added and the mixture heated to 70° C. The pH was adjusted to 10 with acetic acid. Solvent was removed by distillation under nitrogen until the pot temperature reached 103° C. The mixture was cooled to 25° C. Toluene (0.74 L) and water (0.49 L) was added and the mixture heated to 33° C. The layers were separated and the aqueous re-extracted with toluene (0.20 L). The combined toluene solutions were combined, dried over sodium sulfate and filtered to produce a 13 solution of 1.057 L. Assuming quantitative conversion, this solution contains 165 g of 13.

PART D:
Preparation of 14; 5-carboxaldehydeindazole.
Preparation of 5-bromoindazole.

A flask containing 4-bromo-2-methylaniline (95.0 g) in chloroform (0.70 L) was treated with acetic anhydride (0.109 L) at <40° C. The solution was stirred for 50 minutes and potassium acetate (14.6 g) and isoamyl nitrite (0.147 L) was charged. The solution was refluxed at 68° C. for 20 h. The temperature was cooled to 25° C. and the volatiles distilled at 30 mmHg vacuum (T=30–40° C.). Once most of the solvents had distilled, a total of 225 mL of water was charged in portions and the azeotrope of water and the various volatiles distilled. The product mass was transferred back into the reaction vessel using water (50 mL) and concentrated hydrochloric acid (400 mL) charged. The mixture was heated to 50–55° C. and another 100 mL acid charged in portions over 2 h. The solution was cooled to 20° C. and 50% sodium hydroxide (520 g) was charged at <37° C. to bring the pH to 11. Water (100 mL) and ethyl acetate (350 mL) was added and the mixture filtered through a Celite pad. The layers were separated and the aqueous phase further extracted with ethyl acetate (2×200 mL). The combined organic layers were mixed with brine (240 mL), filtered through a Celite pad and separated. The organic solution was dried over magnesium sulfate (3 g) and filtered through a silica gel pad (45 g) with ethyl acetate. The eluant was concentrated by rotary evaporation, adding a total of 0.45 L of heptane during the distillation and continueing until only dry solids remain. The solids were slurried with heptane (0.1 L), filtered and dried under vacuum at 45° C. to produce 91.9 g of 5-bromoindazole (94% yield).

Preparation of 5-carboxaldehydeindazole.

A flask was charged with 60% sodium hydride in mineral oil (20.5 g) and tetrahydrofuran (1.05 L) under nitrogen. A solution of 5-bromoindazole (91.0 g) in tetrahydrofuran (0.64 L) was added over 15 minutes and the mixture stirred another 15 minutes before cooling to −60° C. A solution of 1.3 N sec-buthyllithium in cyclohexane (0.750 L) was added at −60 to −40° C. over 19 minutes. The solution was stirred another hour at −40 to −50° C. A solution of dimethylformamide (160 mL) in tetrahydrofuran (200 mL) was charged at −45 to −40° C. over 12 minutes. The mixture was warmed to 25° C. over 5 h and recooled to 0° C. 1 N Hydrochloric acid (1.20 L) was added at <10° C. and the solution was made basic by adding back solid sodium bicarbonate. The layers were separated and the aqueous further extracted with ethyl acetate (2×0.65 L). The combined organic layers were washed with water (0.35 L). 5-Carboxaldehydeindazole, 14, was extracted from the organic solution by washes with 0.6 N sodium bisulfite solution in water (3×0.65 L). The combined extracts were backwashed with ethyl acetate (0.225 L) and the pH was adjusted to 10 by the addition of 5 N sodium hydroxide (0.21 L used). 5-Carboxaldehydeindazole was extracted into ethyl acetate (3×0.50 L). The combined extracts were dried over magnesium sulfate (3 g) and filtered through a pad of silica gel (50 g) with ethyl acetate. The eluant was concentrated by rotary evaporation, adding a total of 0.30 L heptane during the distillation. The solid was filtered, washed with heptane (0.50 L) and dried under vacuum at 45° C. to produce 54.6 g of 14 (78% yield). The solids contain 2 wgt % ethyl acetate.

PART E:
Preparation of 15.

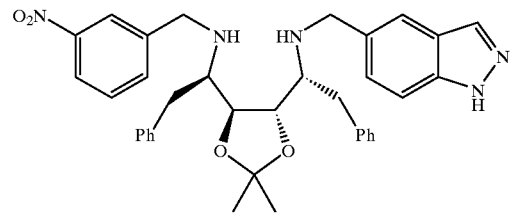

15

A flask equipped with a distillation head was charged with 13 (87.7 g), 14 (27.0 g) and toluene (0.665 L). The mixture was heated and a total of 1.20 L distillate collected. The volume was kept constant by the addition of more toluene. At this point, the distillation head was replaced by a Dean-Stark trap and the mixture refluxed for another 3 h. During this period, added another 0.44 g of 14 in portions. The mixture was cooled to 0° C. Acetic acid (12.7 mL) and sodium triacetoxyborohydride (59.1 g) were added, and the mixture was stirred overnight. Water (0.375 L) was added to quench remaining hydride and the pH was adjusted to 8.3 with 5 N sodium hydroxide (70 mL). Ethyl acetate (0.375 L) was added, the mixture agitated and the layers separated. The aqueous phase was re-extracted with ethyl acetate (0.15 L) and the combined organic layers dried over magnesium sulfate (5 g). The solution was filtered through a pad of silica gel (20 g) and eluted with more ethyl acetate. Toluene (0.20 L) was added and the solution concentrated by rotary evaporation to 123.0 g of orange oil containing 15 (91% yield). The oil contains 17 wgt % toluene.

PART F:
Preparation of 16.

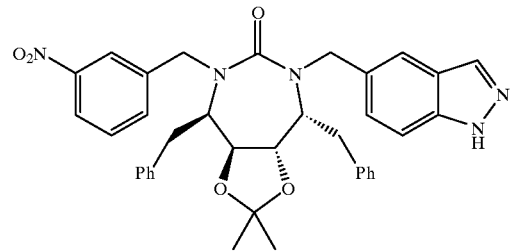

16

A flask equipped with a Dean-Stark trap was charged with 15 (40.0 g), tris[hydroxymethyl]aminomethane (55.3 g) and toluene (1.10 L). The mixture was brought to reflux while a solution of phosgene (8.3 g) in toluene (638 mL) was continuously added over 4 h. At the 2 h mark, another 5.2 g of tris[hydroxymethyl]aminomethane in 20 mL toluene was added. The reaction mixture was concentrated by rotary evaporation and the residue extracted into ethyl acetate (0.40 L). The solution was washed with water (2×0.10 L). Remaining solids were dissolved into water (1.00 L) and further extracted with ethyl acetate (0.20 L). The combined organic layers were filtered through a pad of silica gel (50 g), concentrated by rotary evaporation and further dried under high vacuum to 44.0 g of crude 16. This was purified by flash chromatography on silica gel (40:1 ratio silica gel to crude 16) using ethyl acetate:heptane 2:3. Only fractions clean by TLC were combined. This lot was purified along with several others but had it been done separately, 22.9 g of 16 (55% yield) would have been recovered. The solid contains 5 wgt % ethyl acetate.

PART G:
Preparation of 17.

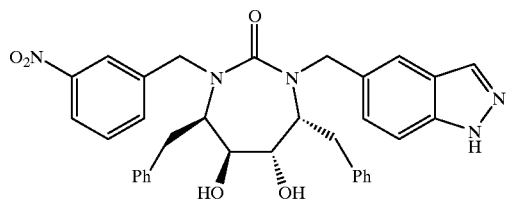

A flask was charged with methanol (0.725 L) and concentrated hydrochloric acid (1.0 mL). Solid 16 (23.4 g) was added in portions to the stirred solution over 5 minutes, followed by concentrated hydrochloric acid (25.0 mL) over 5 minutes. After 30 minutes of stirring, the solution was cooled to 15° C. and solid sodium bicarbonate (30 g) along with aqueous sodium bicarbonate (3 mL) was added to render the mixture slightly basic. The mixture was concentrated by rotary evaporation and mixed with ethyl acetate (0.40 L) and water (0.20 L). The layers were separated and the aqueous layer further extracted with ethyl acetate (50 mL). The combined organic layers were washed with water (50 mL), dried over magnesium sulfate (5 g), filtered through a pad of silica gel (25 g) and concentrated by rotary evaporation. The foam was dried under high vacuum to 23.7 g of 17 (>99% yield). The foam contains 8 wgt % ethyl acetate.

PART H:
Preparation of (I).

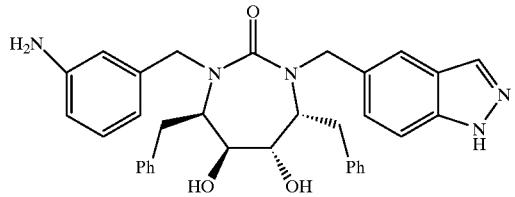

A large pressure bottle was charged with 17 (28.8 g), methanol (0.665 L), acetic acid (41 mL) and 10% palladium on carbon (6.6 g). Oxygen was removed by nitrogen/vacuum cycles and the mixture was pressurized with hydrogen gas to 20 psi. The mixture was shook for 5.5 h while maintaining the hydrogen pressure. The mixture was filtered through a Celite pad and concentrated by rotary evaporation to an oil. This was dissolved into ethyl acetate (0.50 L) and neutralized with a combination of solid sodium bicarbonate and water (0.20 L). The layers were separated and the aqueous phase re-extracted with ethyl acetate (0.10 L). The combined organic layers were dried over magnesium sulfate (5 g), filtered and concentrated by rotary evaporation. The foam was dried under high vacuum to 27.5 g of (I) (95% yield). This foam contains 6 wgt % ethyl acetate.

Utility

The compound of Formula (I) possesses HIV protease inhibitory activity and is therefore useful as an antiviral agent for the treatment of HIV infection and associated diseases. The compound of Formula (I) possesses HIV protease inhibitory activity and is effective as an inhibitor of HIV growth. The ability of the compound of the present invention to inhibit viral growth or infectivity is demonstrated in standard assay of viral growth or infectivity, for example, using the assay described below.

The compound of Formula (I) of the present invention is also useful for the inhibition of HIV in an ex vivo sample containing HIV or expected to be exposed to HIV. Thus, the compound of the present invention may be used to inhibit HIV present in a body fluid sample (for example, a serum or semen sample) which contains or is suspected to contain or be exposed to HIV.

The compound provided by this invention is also useful as a standard or reference compound for use in tests or assays for determining the ability of an agent to inhibit viral clone replication and/or HIV protease, for example in a pharmaceutical research program. Thus, the compound of the present invention may be used as a control or reference compound in such assays and as a quality control standard. The compound of the present invention may be provided in a commercial kit or container for use as such standard or reference compound.

Since the compound of the present invention exhibits specificity for HIV protease, the compound of the present invention may also be useful as a diagnostic reagent in diagnostic assays for the detection of HIV protease. Thus, inhibition of the protease activity in an assay (such as the assays described herein) by the compound of the present invention would be indicative of the presence of HIV protease and HIV virus.

As used herein "$\mu$g" denotes microgram, "mg" denotes milligram, "g" denotes gram, "$\mu$L" denotes microliter, "mL" denotes milliliter, "L" denotes liter, "nM" denotes nanomolar, "$\mu$M" denotes micromolar, "mM" denotes millimolar, "M" denotes molar and "nm" denotes nanometer. "Sigma" stands for the Sigma-Aldrich Corp. of St. Louis, Mo.

HIV RNA Assay

DNA Plasmids and in vitro RNA transcripts:

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the A260.

Probes:

Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 889–912 of HXB2 and the pol biotinylated capture probe (5'-biotin-CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau Nucleic Acids Research 1984, 12, 387). The reporter probes were prepared as 0.5 $\mu$M stocks in 2×SSC (0.3 M NaCl, 0.03 M sodium citrate), 0.05 M Tris pH 8.8, 1 mg/mL BAA. The biotinylated capture probes were prepared as 100 $\mu$M stocks in water.

Streptavidin Coated Plates:

Streptavidin coated plates were obtained from Du Pont Biotechnology Systems (Boston, Mass.).

Cells and Virus Stocks:

MT-2 and MT-4 cells were maintained in RPMI 1640 supplemented with 5% fetal calf serum (FCS) for MT-2 cells or 10% FCS for MT-4 cells, 2 mM L-glutamine and 50 $\mu$g/mL gentamycin, all from Gibco. HIV-1 RF was propagated in MT-4 cells in the same medium. Virus stocks were prepared approximately 10 days after acute infection of MT-4 cells and stored as aliquots at −70° C. Infectious titers of HIV-1(RF) stocks were 1–3×10$^7$ PFU (plaque forming units)/mL as measured by plaque assay on MT-2 cells (see below). Each aliquot of virus stock used for infection was thawed only once.

For evaluation of antiviral efficacy, cells to be infected were subcultured one day prior to infection. On the day of infection, cells were resuspended at 5×10$^5$ cells/mL in RPMI 1640, 5% FCS for bulk infections or at 2×10$^6$/mL in Dulbecco's modified Eagles medium with 5% FCS for infection in microtiter plates. Virus was added and culture continued for 3 days at 37° C.

HIV RNA Assay:

Cell lysates or purified RNA in 3 M or 5 M GED were mixed with 5 M GED and capture probe to a final guanidinium isothiocyanate concentration of 3 M and a final biotin oligonucleotide concentration of 30 nM. Hybridization was carried out in sealed U bottom 96 well tissue culture plates (Nunc or Costar) for 16–20 hours at 37° C. RNA hybridization reactions were diluted three-fold with deionized water to a final guanidinium isothiocyanate concentration of 1 M and aliquots (150 $\mu$L) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 $\mu$l of a hybridization cocktail containing 4×SSC, 0.66% Triton X 100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 $\mu$L of 0.2 mM 4-methylumbelliferyl phosphate (MUBP, JBL Scientific) in buffer$\delta$ (2.5 M diethanolamine pH 8.9 (JBL Scientific), 10 mM MgCl$_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nM.

Microplate Based Compound Evaluation in HIV-1 Infected MT-2 Cells:

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 $\mu$L) were added to a final concentration of 5×10$^5$ per mL (1×10$^5$ per well). Cells were incubated with compounds for 30 minutes at 37° C. in a CO$_2$ incubator. For evaluation of antiviral potency, an appropriate dilution of HIV-1 (RF) virus stock (50 $\mu$L) was added to culture wells containing cells and dilutions of the test compounds. The final volume in each well was 200 $\mu$L. Eight wells per plate were left uninfected with 50 $\mu$L of medium added in place of virus, while eight wells were infected in the absence of any antiviral compound. For evaluation of compound toxicity, parallel plates were cultured without virus infection.

After 3 days of culture at 37° C. in a humidified chamber inside a CO$_2$ incubator, all but 25 $\mu$L of medium/well was removed from the HIV infected plates. Thirty seven $\mu$L of 5 M GED containing biotinylated capture probe was added to the settled cells and remaining medium in each well to a final concentration of 3 M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 $\mu$L of this diluted mixture was transferred to a streptavidin coated microtiter plate. HIV RNA was quantitated as described above. A standard curve, prepared by adding known amounts of PDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an IC$_{90}$ value (concentration of compound required to reduce the HIV RNA level by 90%) for dideoxycytidine (ddC) of 0.2 $\mu$g/mL. IC$_{90}$ values of other antiviral compounds, both more and less potent than ddC, were reproducible using several stocks of HIV-1 (RF) when this procedure was followed. This concentration of virus corresponded to ~3×10$^5$ PFU (measured by plaque assay on MT-2 cells) per assay well and typically produced approximately 75% of the maximum viral RNA level achievable at any virus inoculum. For the HIV RNA assay, IC$_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The IC$_{90}$ for ddC, determined in each assay run, should be between 0.1 and 0.3 $\mu$g/mL. Finally, the plateau level of viral RNA produced by an effective protease inhibitor should be less than 10% of the level achieved in an uninhibited infection. A compound was considered active if its IC$_{90}$ was found to be less than 1 $\mu$M.

The IC$_{90}$ for the compound of Example 1 was determined to be less than 50 nM.

For antiviral potency tests, all manipulations in microtiter plates, following the initial addition of 2× concentrated compound solution to a single row of wells, were performed using a Perkin Elmer/Cetus ProPette.

Dosage and Formulation

The antiviral compound of this invention can be administered as treatment for viral infections by any means that produces contact of the active agent with the agent's site of action, i.e., the viral protease, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

Combination of components (a) and (b)

The therapeutic agent component of this invention can independently be in any dosage form, such as those described above, and can also be administered in various ways, as described above. In the following description component (b) is to be understood to represent one or more agents as described previously. Thus, if components (a) and (b) are to be treated the same or independently, each agent of component (b) may also be treated the same or independently.

Components (a) and (b) of the present invention may be formulated together, in a single dosage unit (that is, combined together in one capsule, tablet, powder, liquid, etc.) as a combination product. When component (a) and (b) are not formulated together in a single dosage unit, component (a) may be administered at the same time as component (b) or in any order; for example component (a) of this invention may be administered first, followed by administration of component (b), or they may be administered in the reverse order. If component (b) contains more that one agent, e.g., one RT inhibitor and one protease inhibitor, these agents may be administered together or in any order. When not administered at the same time, preferably the administration of component (a) and (b) occurs less than about one hour apart. Preferably, the route of administration of component (a) and (b) is oral. The terms oral agent, oral inhibitor, oral compound, or the like, as used herein, denote compounds which may be orally administered. Although it is preferable that component (a) and component (b) both be administered by the same route (that is, for example, both orally) or dosage form, if desired, they may each be administered by different routes (that is, for example, one component of the combination product may be administered orally, and another component may be administered intravenously) or dosage forms.

As is appreciated by a medical practitioner skilled in the art, the dosage of the combination therapy of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

The proper dosage of components (a) and (b) of the present invention will be readily ascertainable by a medical practitioner skilled in the art, based upon the present disclosure. By way of general guidance, typically a daily dosage may be about 100 milligrams to about 1.5 grams of each component. If component (b) represents more than one compound, then typically a daily dosage may be about 100 milligrams to about 1.5 grams of each agent of component (b). By way of general guidance, when the compounds of component (a) and component (b) are administered in combination, the dosage amount of each component may be reduced by about 70–80% relative to the usual dosage of the component when it is administered alone as a single agent for the treatment of HIV infection.

The combination products of this invention may be formulated such that, although the active ingredients are combined in a single dosage unit, the physical contact between the active ingredients is minimized. In order to minimize contact, for example, where the product is orally administered, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines.

Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose or other appropriate materials as known in the art, in order to further separate the active components. The polymer coating serves to form an additional barrier to interaction with the other component. In each formulation wherein contact is prevented between components (a) and (b) via a coating or some other material, contact may also be prevented between the individual agents of component (b).

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time or concurrently by the same manner, will be readily apparent to those skilled in the art, based on the present disclosure.

Pharmaceutical kits useful for the treatment of HIV infection, which comprise a therapeutically effective amount of a pharmaceutical composition comprising a compound of component (a) and one or more compounds of component (b), in one or more sterile containers, are also within the ambit of the present invention. Sterilization of the container may be carried out using conventional sterilization methodology well known to those skilled in the art. Component (a) and component (b) may be in the same sterile container or in separate sterile containers. The sterile containers of materials may comprise separate containers, or one or more multi-part containers, as desired. Component (a) and component (b), may be separate, or physically combined into a single dosage form or unit as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

Obviously, numerous modifications and variations of the present invention are possible in light of the above teachings. It is therefore to be understood that within the scope of the appended claims, the invention may be practiced otherwise than as specifically described herein.

What is claimed is:

1. A compound of Formula (I):

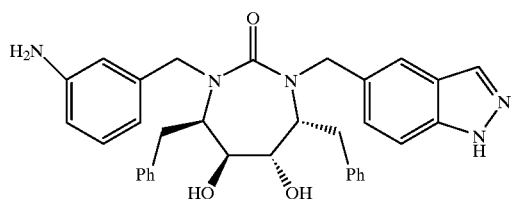

or a pharmaceutically acceptable salt thereof.

2. A pharmaceutical composition comprising a pharmaceutically acceptable carrier and a therapeutically effective amount of a compound of claim 1 or a pharmaceutically acceptable salt thereof.

3. A method for treating HIV infection which comprises administering to a host in need of such treatment a therapeutically effective amount of a compound of claim 1 or a pharmaceutically acceptable salt thereof.